United States Patent [19]

Kiekens et al.

[11] Patent Number: 5,478,708
[45] Date of Patent: Dec. 26, 1995

[54] NEW DYES FOR USE IN DIVERSE APPLICATIONS

[75] Inventors: Eric Kiekens, Kessel-Lo; Paul Callant, Edegem, both of Belgium

[73] Assignee: AGFA-Gevaert, N.V., Mortsel, Belgium

[21] Appl. No.: 345,739

[22] Filed: Nov. 21, 1994

[30] Foreign Application Priority Data

Dec. 2, 1993 [EP] European Pat. Off. .............. 93203382
Feb. 28, 1994 [EP] European Pat. Off. .............. 94200500

[51] Int. Cl.$^6$ .................................................. G03C 1/825
[52] U.S. Cl. .................. 430/517; 430/510; 430/507; 430/522; 430/139; 548/360.5; 548/363.1
[58] Field of Search ..................... 430/510, 507, 430/517, 522, 139; 548/360.5, 363.1

[56] References Cited

U.S. PATENT DOCUMENTS

| | | | |
|---|---|---|---|
| 3,560,214 | 2/1971 | Ruda | 430/522 |
| 4,857,446 | 8/1989 | Diehl et al. | 430/510 |
| 5,344,749 | 9/1994 | Kiekens et al. | 430/517 |

FOREIGN PATENT DOCUMENTS 0385461  9/1990  European Pat. Off. .............. 430/517

*Primary Examiner*—Thomas R. Neville
*Attorney, Agent, or Firm*—Breiner & Breiner

[57] ABSTRACT

The synthesis and the application of new dyes is described. In particular said new dyes can be incorporated in non-migratory state in hydrophilic colloid layers of photographic materials wherefrom they can be rapidly removed after being quickly decolorized in alkaline aqueous liquids used in the processing of said materials. In photographic applications dyes of the general formula (I) are provided with at least one ionizable group which permits solubilization in aqueous and/or alkaline medium.

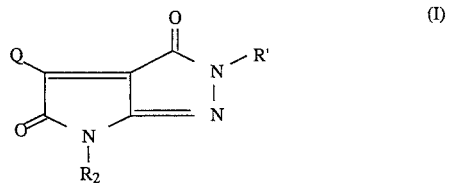

7 Claims, No Drawings

5,478,708

NEW DYES FOR USE IN DIVERSE APPLICATIONS

DESCRIPTION

1. Field of the Invention

The present invention relates to a new class of dyes and their applications.

2. Background of the Invention

Dyes may be used for the dyeing of several very different materials like e.g. natural and synthetic fibers, textiles, plastics and leather. Dyes may be used further as acid-base indicators, as biological stains, as filter dyes, antihalation dyes or dyes providing more sharp images in photographic applications, for information recording, printing inks, camouflage, as light-collecting elements, for the colouring of food, as an analytical reagent, as a transfer dye in dye-transfer photographic materials and in many other applications.

In photography dyes may be divided into spectrally and non-spectrally sensitizing dyes, indicating whether the dyes are adsorbed or not at the surface of the light-sensitive silver halide crystals used in photographic elements.

Non-spectrally sensitizing dyes e.g. are widely used in a photosensitive silver halide emulsion layer as screening dyes, in an undercoat adjacent to the photosensitive layer and/or in a backing layer on the side of the support opposite to the photosensitive layer(s) to absorb reflected and scattered light. Its function as antihalation dye or in an overcoat or interlayer to shield a particular photosensitive layer against undesired exposure being therefore referred to as filter or absorber dye is highly appreciated. The adjustment of the sensitivity of a photographic element as required in the production specifications is another application.

For example in order to improve image sharpness an absorber dye can be present in one or more filter layers between silver halide emulsion layers that are coated at opposite sides of a transparent film support of an X-ray recording material. The imagewise exposure of said recording material proceeds in a cassette between a pair of X-ray intensifying screens that each are held in contact with an adjacent silver halide emulsion layer. By said arrangement the imaging light that would cross the support and to some extent becomes scattered thereby, is considerably attenuated and cannot give rise to an unsharp image in an opposite silver halide emulsion layer.

Spectrally the dye absorption spectrum should approximately be equal to the sensitivity spectrum of the corresponding silver halide emulsion in the layer of which a sharp image has to be reproduced.

On the one hand it is very important that filter dyes remain, i.e. that they are non-migratory, in the layer wherein they have been incorporated especially when this layer is in direct contact with the silver halide emulsion layer in order to prevent a desensitizing action on the silver halide. On the other hand the filter dyes may not stain the photographic material after image processing. Therefore preference is given to filter dyes that decolorize or can be removed from the photographic element in the processing stage. This requirement is nowadays becoming more and more stringent as rapid processing times are of increasing interest.

As described in U.S. Pat. No. 3,560,214 dyes comprising a carboxyl and phenyl substituted pyrazoline nucleus linked through a methine group to a dialkylaminophenyl group can be removed relatively easily in alkaline aqueous processing liquids but lack sufficient fastness to diffusion in hydrophilic colloid layers.

Other filter dyes characterized by the presence of a 2-pyrazolin-5-one nucleus substituted with a carboxyphenyl group and including a methine group or chain linked to a dialkylamino group are described in U.S. Pat. No. 4,857,446.

Recently in EP-Application 92.202.767 the synthesis and the application of new dyes has been described, wherein the filter dyes have an amide function or a derivative therefrom as a substituent at the mono- or trimethine chain. When said new dyes are incorporated in the non-migratory state in hydrophilic colloid layers of photographic materials they can be rapidly removed after being quickly decolourized under the influence of sulphite ions in alkaline aqueous liquids used in the processing of said materials.

As is well-known the monomethine dyes have an absorption spectrum of which the maximum is in the shorter wavelength range of the visible spectrum so that normally a second filter dye is needed to block or absorb green light and even a third one to absorb radiations of longer wavelengths, e.g. radiations in the red or even in the infrared region. Another aspect concerning decolouration under the influence of sulphite ions in alkaline aqueous liquids is related to the decreasing reaction velocity with sulphite ions going from mono- to trimethine dyes.

Once a filter dye has been selected, the problem is how to get the filter dye in a coated layer so that all the requirements mentioned previously are met.

One of the possibilities is to make use of solid particle dispersions of water insoluble dyes as has been described in EP 0,384,633 A2; EP 0,323,729 A2; EP 0,274,723 B1, EP 0,276,566 B1, EP 0,351,593 A2 and U.S. Pat. Nos. 4,900,653; 4,904,565; 4,949,654; 4,940,654; 4,948,717; 4,988,611 and 4,803,150.

Another possibility is offered in Research Disclosure 19551 (July 1980) which describes an approach of associating hydrophobic compounds with latex polymer particles.

EP 0,401,709 A2 describes the dissolution of hydrophobic dyes into oil droplets being substantially insoluble in water and the preparation of the corresponding oil former dispersions or loaded polymer latex dispersions.

To prevent dye wandering, the dye is often coated with a mordant to bind the dye in the layer in which it is coated as is e.g. illustrated in U.S. Pat. No. 2,527,583. As dye mordants polymers are often used.

Another possibility is offered by adsorption of dyes at the surface of very fine light-insensitive silver halide crystals with the expectable disadvantages of the coating of more silver halide crystals and possibly fixation difficulties.

Very few dyes satisfy the above requirements especially when rapid processing is concerned. Moreover, apart from the requirement of non-diffusibility and of rapid decolourizing or removal by rapid processing that the dyes should meet, they should have high stability in the photographic material, not only under the influence of the ingredients present in the emulsion layers prior to coating, but especially under severe storage conditions of the packed material e.g. under circumstances of high temperatures and high degrees of humidity.

OBJECTS AND SUMMARY OF THE INVENTION

It is an object of the present invention to provide new dyes suitable for diverse applications. In particular it is an object of this invention to provide non-spectrally sensitizing dyes that can be incorporated in non-migratory state in hydrophilic colloid layers of photographic materials wherefrom they can be rapidly removed in alkaline aqueous liquids used in the processing of said materials.

It is a further object of the invention to provide new dyes providing high density in the required spectral region, thereby reducing the scattering of incident light in photographic elements.

Other objects will become apparent from the description hereinafter.

In accordance with the present invention dyes are provided corresponding to the following general formula (I):

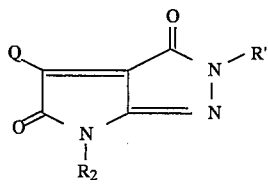
(I)

wherein Q represents a substituted or unsubstituted aromatic or heterocyclic aromatic ring and wherein $R^1$ and $R^2$ each independently represent hydrogen, substituted or unsubstituted alkyl; substituted or unsubstituted aryl; substituted or unsubstituted heterocyclyl; substituted or unsubstituted vinyl or one of the following substituents being $C(=N-R^3)-R^4$; $CH=(N+)(-R^5)_2$; $CR^3=(N+)(-R^4)_2$; $C=N^+-O^-$; CO—H and the acetals and thioacetals derived therefrom; $CO-NH-R^5$; $CO-NH-SO_2-R^5$ and the corresponding salts; $CO-O-R^5$; $CO-R^5$ and the acetals, thioacetals, animals and 1,3-oxathiolans derived therefrom; $CO-S-R^5$; CS—H; $CS-NH-R^5$; $CS-O-R^5$; $CS-R^5$; $CS-S-R^5$; F, Cl, Br, I, CN; $N=C=N-R^5$; $N=C=O$; $N=C=S$; $N=N(O)-R^5$; $N=N-R^5$; $NH-CO-NH-R^5$; $NH-CO-R^5$; $NH-CS-NH-R^5$; $NH-CS-R^5$; $NH-R^5$; $NH-SO_2-R^5$; $NO_2$; $NR^3-CO-R^4$; $NR^1-CS-R^2$; $NR^5{}_2$; O—CN; $O-CO-R^5$;$O-R^5$; $O-SO_2-R^5$; $P(OR^5)_2$; $PO-(OR^5)_2$; S—CN; $S-CO-R^5$; $S-CS-R^5$; $S-R^5$; $S-R^5$; $SO-R^5$; $SO_2-NHR^5$ and the salts derived therefrom; $SO_2-R^5$; $SO_3H$ and the salts derived therefrom and wherein each of $R^3$, $R^4$ and $R^5$ independently represent hydrogen; substituted or unsubstituted alkyl; substituted or unsubstituted aryl; substituted or unsubstituted heterocyclyl; substituted or unsubstituted vinyl and the like.

In accordance with the present invention a photographic element is provided comprising a support and at least one photo-sensitive silver halide emulsion layer, wherein said element comprises, dispersed in a hydrophilic water-permeable colloid binder, e.g. gelatin, at least one dye according to the above general formula.

Further in accordance with the present invention a photographic element is provided comprising a support and at least one photo-sensitive silver halide emulsion layer, wherein said element comprises said at least one dye according to the above formula in a solid particle state.

DETAILED DESCRIPTION OF THE INVENTION

In a preferred embodiment in the general formula (I) Q is an aromatic group corresponding to the general formula (II)

(II)

wherein X represents NRR', OR, SR wherein R and R' are substituted or unsubstituted alkyl or aryl, R and R' each independently represent substituted or unsubstituted alkyl or aryl, or wherein R and R' are forming a ring or each form a ring with $R^9$, wherein $R^9$ represents hydrogen; substituted or unsubstituted alkyl; substituted or unsubstituted aryl; substituted or unsubstituted heterocyclyl; substituted or unsubstituted vinyl and the like, this list being not limitative.

Dyes according to this invention show the presence of a pyrrolo[2,3-c] pyrazolone ring. The presence of this group clearly affects the spectral behaviour, shifting the absorption to longer wavelengths. Particularly in photographic materials the dyes according to this invention are decolourized quickly enough, as required in rapid processing conditions. Especially for 38 s processing cycles the dyes according to this invention, containing one or more ionizable groups, are used advantageously. The said ionizable groups make the dye become soluble in aqueous and/or in aqueous alkaline medium. A typical example of an aqueous soluble group is $-SO_3H$, whereas characteristic aqueous alkali soluble groups are —COOH, phenolic —OH, sulfonamide, imide, sulfamoyl, acylsulfamoyl, sulfonylcarbamoyl, sulfonimide, carbamoyl-sulfamoyl etc., being not restricted thereto.

The synthesis of dyes according to the present invention may follow different ways as illustrated hereinafter.

A first illustration of the preparation of dyes according to this invention is given by reaction of products A1–A4 with product B in the presence of e.g. $ZnCl_2$ in methoxypropanol as a solvent. Dependant on the required dye structure also catalysts differing from $ZnCl_2$ can be used, such as triethylamine, acetic acid, sodium acetate, piperidine acetate, silica, sodium hydroxide, etc. Moreover whatever a method can be applied that enables the removal of $H_2O$ from the reaction medium. Even "molecular sieves" can be used therefor or e.g. azeotropic destillation techniques that are typically performed in a so-called Dean-Stark apparatus. The formulae of products A1–A4 and product B are given hereinafter.

Product A1

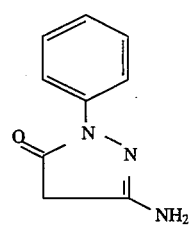

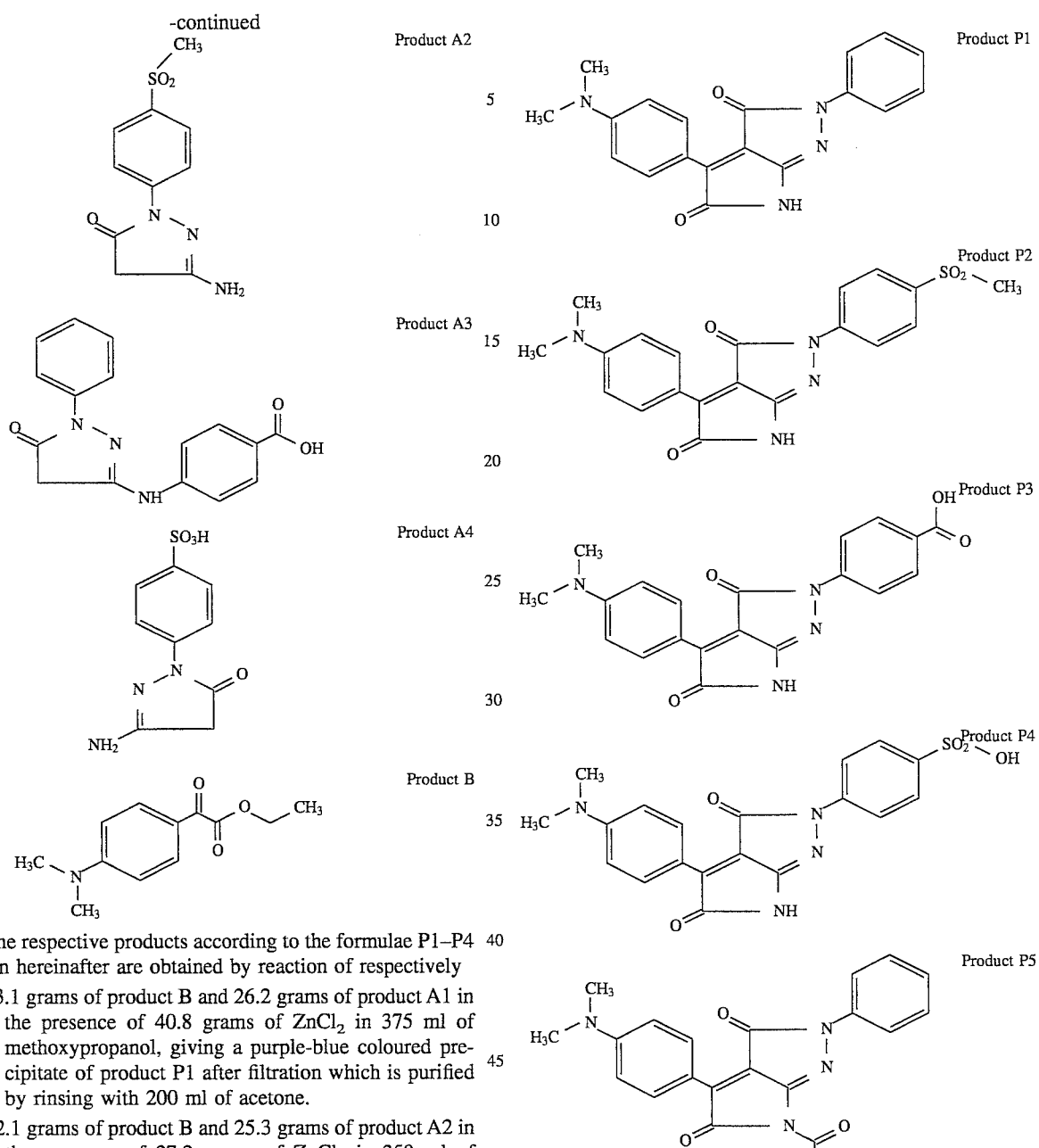

The respective products according to the formulae P1–P4 given hereinafter are obtained by reaction of respectively

- 33.1 grams of product B and 26.2 grams of product A1 in the presence of 40.8 grams of ZnCl$_2$ in 375 ml of methoxypropanol, giving a purple-blue coloured precipitate of product P1 after filtration which is purified by rinsing with 200 ml of acetone.
- 22.1 grams of product B and 25.3 grams of product A2 in the presence of 27.2 grams of ZnCl$_2$ in 250 ml of methoxypropanol, giving a green coloured precipitate of product P2 after filtration which is purified by rinsing with 300 ml of acetone.
- 10.0 grams of product B and 9.9 grams of product A3 in the presence of 12.2 grams of piperidine acetate in 100 ml of methoxypropanol, giving a black precipitate of product P3 after filtration which is purified by rinsing with 100 ml of acetone.
- 10.0 grams of product B and 2.5 grams of product A4 in the presence of 2.7 grams of ZnCl$_2$ in 25 ml of methoxypropanol, giving a green coloured precipitate of product P4 after filtration which is purified by rinsing with 10 ml of acetic acid.

Starting from product P1, product P5 is obtained by refluxing during 2 hours of 90 grams of product P1 in a mixture with 100 ml of acetic anhydride and 50 ml of dimethylacetamide. After cooling the precipitate of product P5 is obtained and purified after filtration and washing with 50 ml of acetone.

Another illustration of the preparation of dyes according to this invention is given by reaction of products A5–A8 with product B in the presence of ZnCl$_2$ in methoxypropanol as a solvent, wherein dependant on the required dye structure also catalysts differing from ZnCl$_2$ can be used as already set forth hereinbefore. The formulae of the said products A5–A8 are given hereinafter:

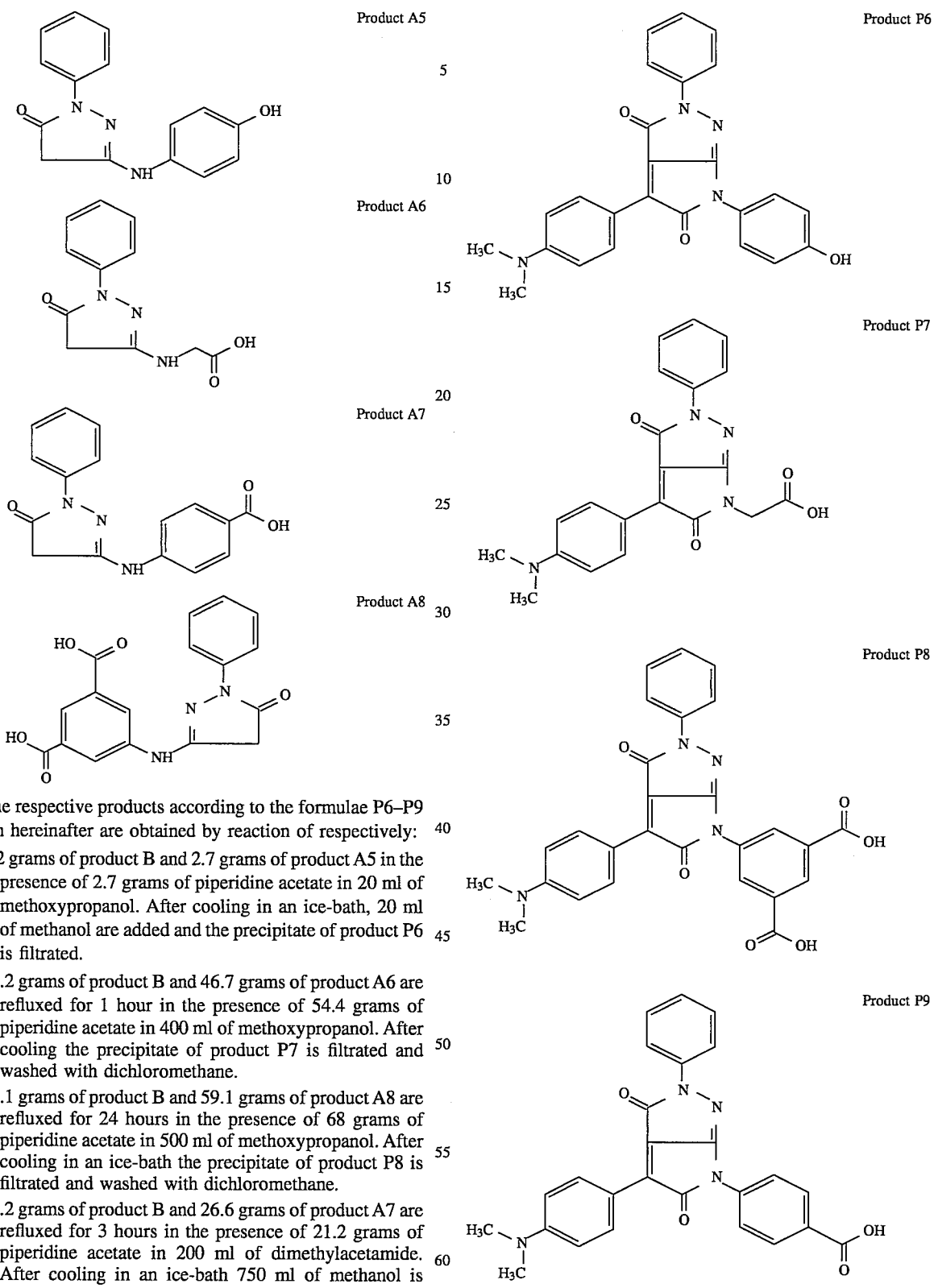

The respective products according to the formulae P6–P9 given hereinafter are obtained by reaction of respectively:

2.2 grams of product B and 2.7 grams of product A5 in the presence of 2.7 grams of piperidine acetate in 20 ml of methoxypropanol. After cooling in an ice-bath, 20 ml of methanol are added and the precipitate of product P6 is filtrated.

44.2 grams of product B and 46.7 grams of product A6 are refluxed for 1 hour in the presence of 54.4 grams of piperidine acetate in 400 ml of methoxypropanol. After cooling the precipitate of product P7 is filtrated and washed with dichloromethane.

22.1 grams of product B and 59.1 grams of product A8 are refluxed for 24 hours in the presence of 68 grams of piperidine acetate in 500 ml of methoxypropanol. After cooling in an ice-bath the precipitate of product P8 is filtrated and washed with dichloromethane.

17.2 grams of product B and 26.6 grams of product A7 are refluxed for 3 hours in the presence of 21.2 grams of piperidine acetate in 200 ml of dimethylacetamide. After cooling in an ice-bath 750 ml of methanol is added, the precipitate of product P9 is filtrated and washed with 300 ml of aceton.

The formulae of products P10–P21 which have been prepared in similar ways are given hereinafter.

Product P10
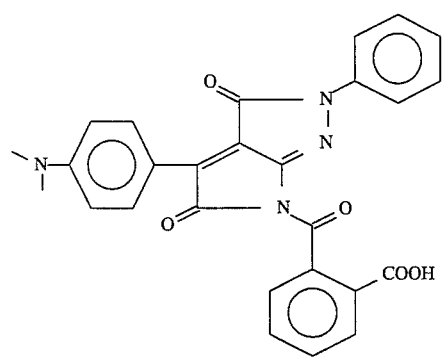
Product P11
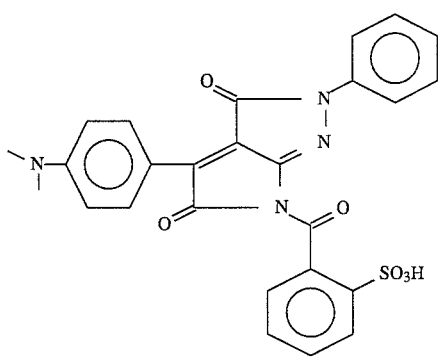
Product P12
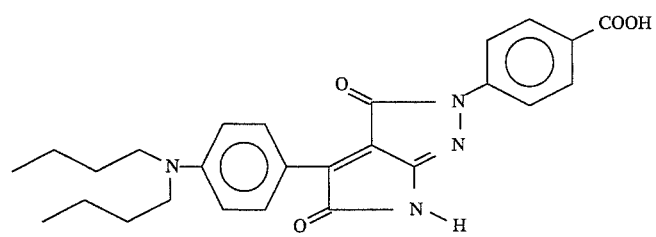
Product P13
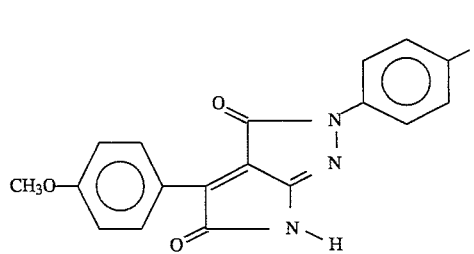
Product P14
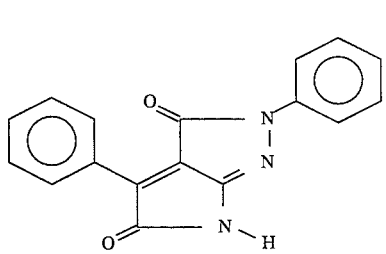
Product P15
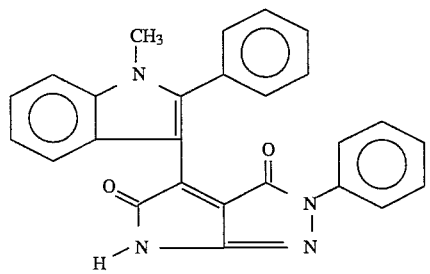
Product P16
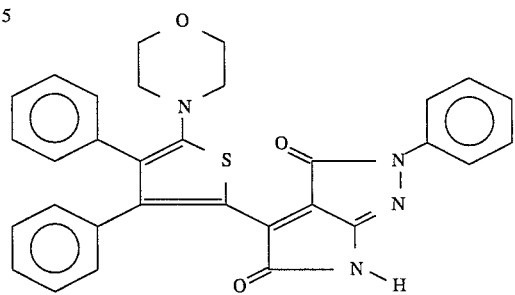
Product P17
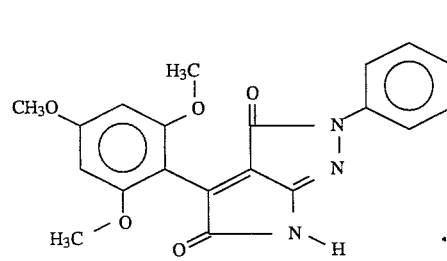
Product P18
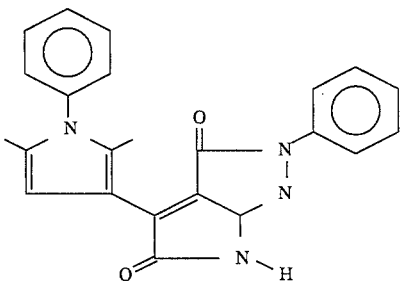
Product P19
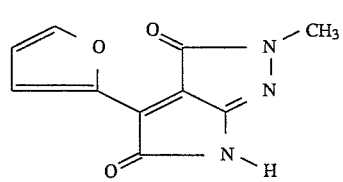

-continued
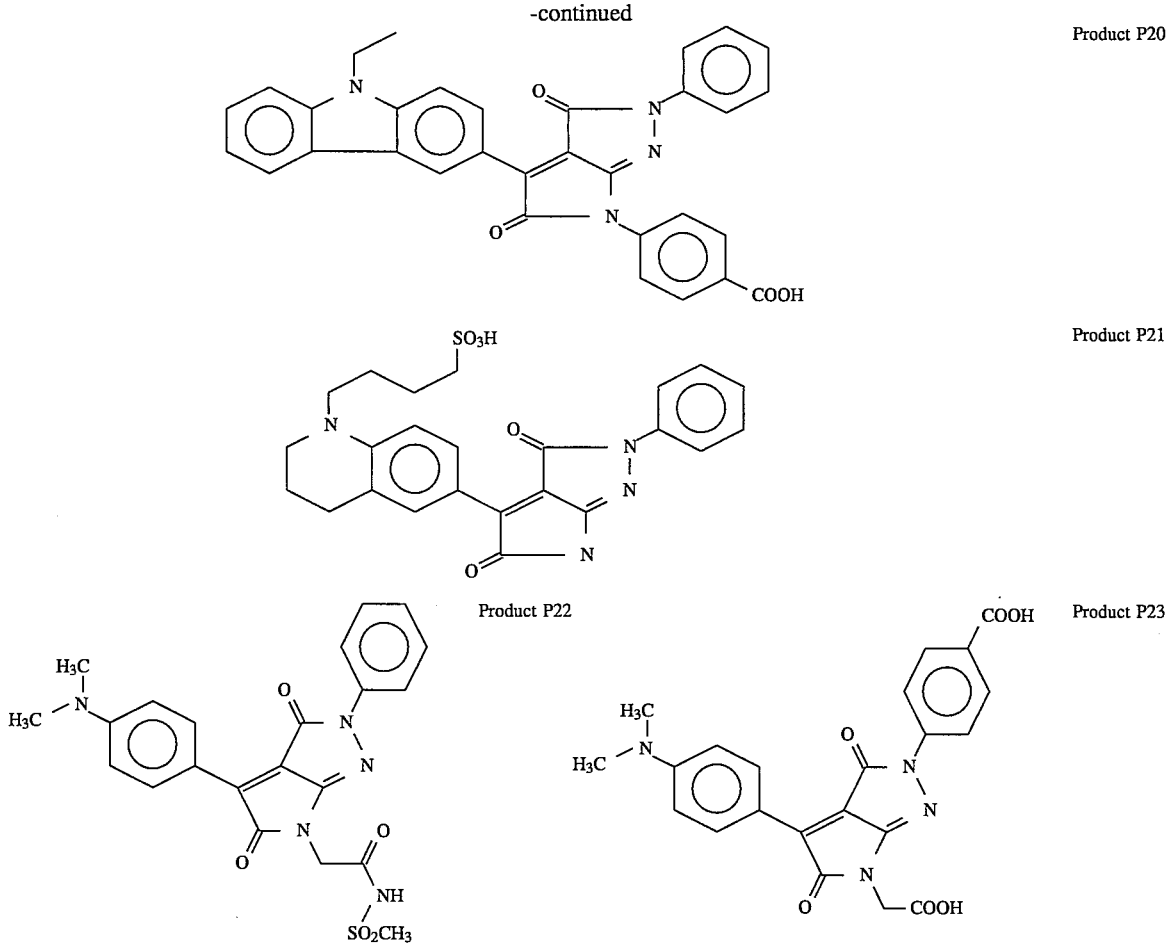
Product P20
Product P21
Product P22
Product P23
The reaction scheme for obtaining Product P23 is given hereinafter.
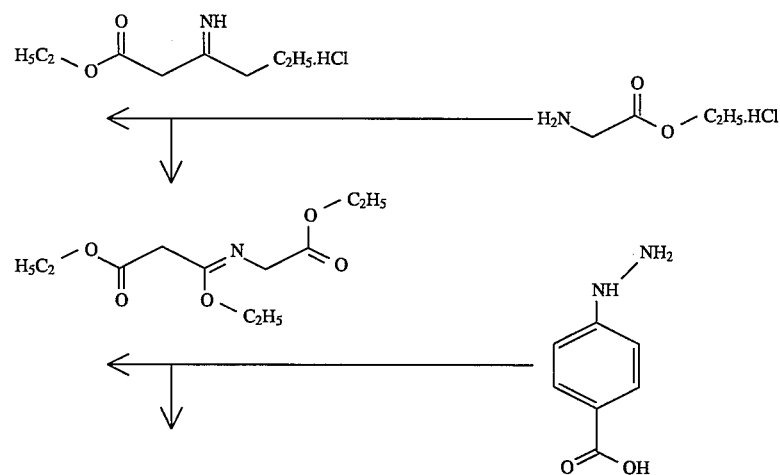

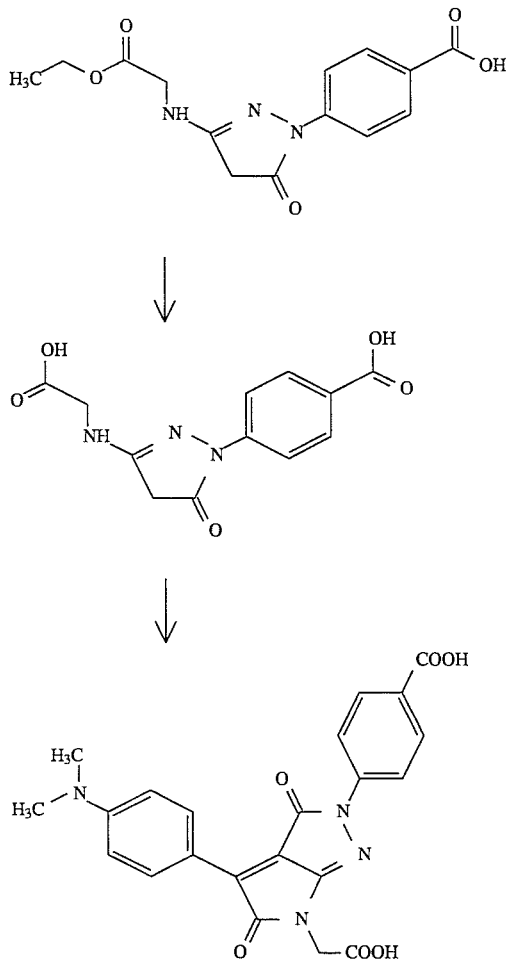

The choice of the substituents may cause a more hypsochromic shift of the absorption spectrum if required: e.g. by replacement of a dimethylamino-group by an alkoxy-group.

From the prior art it is known that the presence of one or more anionic, weakly-acidic groups in the dyes is important to provide sufficient non-migratory character at coating pH values in the range of 4 to 8, which are especially preferred for the coating of photographic materials.

In the acid pH range the filter dyes according to the present invention can be incorporated in aqueous coating compositions in dispersed form by using commercial mixing devices for making colloidal dispersions, e.g. in gelatin. The size of the dye particles obtained is chosen to facilitate coating and rapid decolouration of the dye. Where the dyes are initially crystallized in the form of particles larger than desired for use, conventional techniques for achieving smaller particle sizes can be employed, such as ball milling, roller milling, sand milling and the like. The solid particle dispersions cannot only be prepared in the presence of gelatin as a colloidal medium but also e.g. in colloidal silica. A method of preparing an aqueous solid particle dispersion of a dye according to this invention, for incorporation in one of the layers of a photographic silver halide material may comprise the steps of dissolving a non-watersoluble but alkali-soluble dye in an aqueous alkaline solution, if necessary with the help of an organic water soluble solvent precipitating the said dye from said solution in the presence of colloidal silica sol, preferably in the further presence of a dispersing agent by lowering the pH of the solution, e.g. by neutralizing with an aqueous acidic solution removing water-soluble salts formed by the precipitation and any organic solvent used, and concentrating the dispersion either during or after the precipitation by dialysis or ultrafiltration or after precipitation by flocculation and decantation, followed by washing and further decantation.

Said precipitation in the presence of colloidal silica sol preferably occurs in the further presence of a dispersing agent, like e.g. a 2-N,N,N-trialkylamino-acetic acid and can be performed by simultaneous addition of an aqueous alkaline solution comprising the alkaline-soluble compound and an aqueous acidic solution, to a stirred solution comprising the total or partial amount of colloidal silica sol and of dispersing agent while keeping the pH constant, preferably at a value of less than 6.0, the rest of said amount if any being present in at least one of said solutions.

Preferred dispersing agents used during the preparation of solid silica dispersions are one or more partially ionizable polymer(s) or one or more surfactant(s) or a combination thereof.

Another possibility to obtain ultra fine dye dispersions may consist in acidifying a slightly alkaline coating composition during the preparation of the coating composition or "in situ" just before coating it onto the supporting layer. It has been found that the application of this dosage technique allows us to obtain the dyes in a very fine solid particle form, homogeneously divided into the coated layer so that solid particles can hardly be observed even by means of microscopic techniques.

The non-diffusing dyes the synthesis of which has been described hereinbefore and which are added to a hydrophilic layer of a photographic element as a solid particle have a mean diameter of less than 10 μm, more preferably less than 1 μm and still more preferably less than 0.1 μm.

At a pH of at least 10 the dispersed filter dyes are easily solubilized so that they are removed almost completely from a hydrophilic waterpermeable colloid layer of a photographic silver halide emulsion material by its common alkaline aqueous liquid processing and leave almost no residual stain. The presence of sulfite in the processing solution contributes to a more rapid discoloration of the filter dyes.

Photographic elements with dyes according to this invention in one or more hydrophilic layers are very rapidly discoloured in 38 s processing cycles, comprising a development, fixing, rinsing and drying step as applied in radiography.

The hydrophilic colloidal layer(s) in which the dye(s) are incorporated in accordance with the present invention can be a backing layer, an antihalation undercoat layer, a silver halide emulsion layer, an intermediate layer and a protective outermost-layer. Preferred amounts of dye(s) present in the hydrophilic colloid layer(s) mentioned hereinbefore are in the range of from 0.01 to 1.0 mmole/m$^2$.

Emulsion layers used in accordance with this invention may contain light-sensitive silver halide crystals with a diameter of at least 0.1 μm. In a layer arrangement comprising intermediate layers very fine light-insensitive silver halide particles with a diameter of 10 to 100 nm known as Lippmann emulsions, may be incorporated e.g. to serve as scavangers to prevent oxidized developer products to migrate into adjacent layers.

The layers previously mentioned as suitable layers comprising a filter or antihalation dye may be incorporated in e.g. X-ray materials, graphic arts materials, diffusion transfer materials, black and white or colour cinematographic materials etc.

According to a preferred embodiment the dye or dyes are incorporated in a antihalation back coating layer for single-coated materials or a antihalation undercoating layer or layers, especially for double-coated materials as e.g. X-ray photographic materials.

In an outermost layer or layers or in an emulsion layer or layers one or more dyes according to this invention may be used to adjust the sensitivity of the photographic material as required by the production specifications. So it is possible to apply a dosing feeder just before coating the hydrophilic layer concerned and to control the production of the photographic material in this way, the dye(s) being present in the form of a gelatinous dispersion or in a solid particle state.

Dyes according to this invention absorbing in the green spectral range can be used advantageously between silver halide emulsion layers of double-side coated (duplitized) photographic film material applied in X-ray recording for use with green light emitting X-ray conversion phosphor screens. By said arrangement the green light that would cross the support and to some extent become scattered thereby, is considerably attenuated and cannot give rise to an unsharp image into an opposite silver halide emulsion layer.

Green light emitting phosphor screens and their use in combination with green sensitive silver halide emulsion layers of a double side coated (duplitized) film are described e.g. in U.S. Pat. No. 4,130,428, wherein also several measures, e.g. the use of filter dyes, to reduce cross-over light have been described.

In a particular embodiment of the present invention the dyes are incorporated into a radiographic material that is provided at both sides of the support with a silver halide emulsion layer and an antistress layer as a protective layer coated thereover. The radiographic material preferably has on both sides of the film support silver halide emulsion coatings that are split into two distinctive emulsion layers having silver halide crystals of different average grain size one of which is a high speed emulsion layer and the other is a low speed emulsion layer; the high speed emulsion layer being situated at a larger distance from the support than the low speed emulsion layer. In this way the sensitometric curve can be fine-tuned, giving the perfect profile for the specific application. The layer arrangement may also be opposite to the previously cited sequence in order to get a higher contrast. Moreover even without using a separate anticrossover layer this layer arrangement reduces crossover, especially in the critical low density area. In the presence of crossover preventing antihalation undercoat layers containing the dyes according to this invention the crossover reduction is improved without leaving a colour stain upon processing, especially upon rapid processing in less than 60 seconds, preferably in 38 seconds as a reference processing time of materials with high-throughput.

All combinations of symmetrically double-sized films with a symmetric or asymmetric set of intensifying screens or combinations of double-sized films with asymmetric emulsion layers, whether or not duplitized, in combination with a symmetric or asymmetric set of intensifying screens can be used, depending on the specific needs required.

According to another embodiment the green-light absorbing dyes can be used in a antihalation layer of a photographic silver halide emulsion material in order to improve image sharpness by absorbing exposure light penetrating the emulsion layer(s) into the direction of the support. The use of said mainly green light absorbing dyes in an antihalation layer is particularly advantageous in silver halide emulsion materials that are made spectrally sensitive to green light and of which the exposure proceeds with a green light emitting laser e.g. argon ion laser the main power of which is emitted at 488 and 514 nm.

The dyes according to this invention may not only be used as filter dyes, antihalation dyes or dyes providing more sharp images in photographic applications but also for information recording, printing inks, camouflage, as light-collecting elements, for the colouring of food, as an analytical reagent, as a transfer dye in dye-transfer (photographic) materials and in many other applications.

The dyes according to this invention may further be used for the dyeing of several very different materials like e.g. natural and synthetic fibers, textiles, plastics and leather and may also be used as acid-base indicators, as biological stains etc.

We claim:

1. A photographic material comprising a support and at least one light-sensitive silver halide emulsion layer characterized in that it comprises in a hydrophilic colloid layer at least one dye corresponding to the general formula (I):

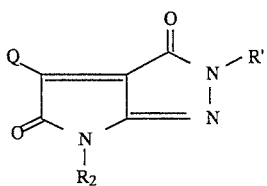

(I)

wherein Q represents an aromatic or a heterocyclic aromatic ring and wherein $R^1$ and $R^2$ each independently represent a member selected from the group consisting of a hydrogen atom, an alkyl; an aryl; a heterocyclyl; a vinyl; $C(=N-R^3)-R^4$; $CH=(N+)(-R^5)_2$; $CR^3=(N+)(-R^4)_2$; $C\equiv N^+-O$; $CO-H$ and the acetals and thioacetals derived therefrom; $CO-NH-R^5$; $CO-NH-SO_2-R^5$ and the corresponding salts; $CO-O-R^5$; $CO-R^5$ and the acetals, thioacetals, animals and 1,3-oxathiolans derived therefrom; $CO-S-R^5$; $CS-H$; $CS-NH-R^5$; $CS-O-R^5$; $CS-R^5$; $CS-S-R^5$; F, Cl, Br, I, CN; $N=C=N-R^5$; $N=C=O$; $N=C=S$; $N=N(O)-R^5$; $N=N-R^5$; $NH-CO-NH-R^5$; $NH-CO-R^5$; $NH-CS-NH-R^5$; $NH-CS-R^5$; $NH-R^5$; $NH-SO_2-R^5$; $NO_2$; $NR^3-CO-R^4$; $NR^1-CS-R^2$; $NR^5_2$; $O-CN$; $O-CO-R^5$; $O-R^5$; $O-SO_2-R^5$; $P(OR^5)_2$; $PO-(OR^5)_2$; $S-CN$; $S-CO-R^5$; $S-CS-R^5$; $S-R^5$; $S-R^5$; $SO-R^5$; $SO_2NHR^5$ and the salts derived therefrom; $SO_2-R^5$; $SO_3H$ and the salts derived therefrom and wherein each of $R^3$, $R^4$ and $R^5$ independently represents a member selected from the group consisting of an alkyl; an aryl; a heterocyclyl and a vinyl.

2. A photographic material according to claim 1 wherein the dye(s) is(are) present in a hydrophilic colloid layer in an amount of 0.01 to 1.0 mmole/m².

3. A photographic material according to claim 1 wherein the dye(s) is(are) present as a gelatinous dispersion(s).

4. A photographic material according to claim 1 wherein the dye(s) is(are) present as solid particle dispersion(s).

5. A photographic material according to claim 1 wherein the dye(s) is(are) present as solid silica particle dispersion(s).

6. A photographic material according to claim 1 wherein said photographic material is an X-ray material.

7. A photographic material according to claim 1 wherein said dye is present in an antihalation undercoat layer between the support and at least one silver halide emulsion layer.

* * * * *